United States Patent [19]

Oh-Kita et al.

[11] Patent Number: 4,968,838

[45] Date of Patent: Nov. 6, 1990

[54] PROCESS FOR THE PREPARATION OF UNSATURATED CARBOXYLIC ACIDS

[75] Inventors: Motomu Oh-Kita; Kazuhiro Ishii; Masaaki Kato; Masao Kobayashi, all of Otake, Japan

[73] Assignee: Mitsubishi Rayon Co., Ltd., Tokyo, Japan

[21] Appl. No.: 296,098

[22] Filed: Jan. 12, 1989

Related U.S. Application Data

[62] Division of Ser. No. 795,820, Nov. 7, 1985, Pat. No. 4,891,347.

[30] Foreign Application Priority Data

Nov. 8, 1984 [JP] Japan ................... 59-234140

[51] Int. Cl.$^5$ ............... C07C 51/25; C07C 57/055
[52] U.S. Cl. ................... 562/534; 502/206; 502/209; 562/535; 260/413
[58] Field of Search ........... 562/535, 534; 260/413; 502/209, 206

[56] References Cited

U.S. PATENT DOCUMENTS

| | | | |
|---|---|---|---|
| 4,118,419 | 10/1978 | Ishii | 562/535 |
| 4,454,346 | 6/1984 | Khoobiar | 562/535 |
| 4,558,029 | 12/1985 | Paparigos et al. | 562/535 |

Primary Examiner—Vivian Garner
Attorney, Agent, or Firm—Armstrong, Nikaido, Marmelstein, Kubovcik & Murray

[57] ABSTRACT

The present invention provides a process for the preparation of a catalyst used in the production of unsaturated carboxylic acids such as methacrylic acid by the gas phase catalytic oxidation of the corresponding unsaturated aldehydes such as methacrolein. Said catalyst is composed of a multi-component composition containing at least phosphorus, molybdenum and antimony. The present invention has attained an improvement in its catalytic performance such as conversion rate, selectivity, single-pass yield, etc. by using antimony trioxide with average particle size of no more than 0.2 micron as a starting material upon preparing said catalyst.

2 Claims, No Drawings

PROCESS FOR THE PREPARATION OF UNSATURATED CARBOXYLIC ACIDS

This is a division of application Ser. No. 795,820 filed 11/7/85, now U.S. Pat. No. 4,891,347.

FIELD OF THE INVENTION

This invention relates to a process for the preparation of a catalyst used in the production of unsaturated carboxylic acids by the gas phase catalytic oxidation of the corresponding unsaturated aldehydes.

DESCRIPTION OF THE PRIOR ART

Numerous processes have been proposed which utilize catalysts containing phosphorus, molybdenum, and antimony in the production of unsaturated carboxylic acids by the gas phase catalytic oxidation of the corresponding aldehydes. Examples include Japanese Patent Publication [Kokoku] No. 13702/81 (catalyst composition: P, Mo, Sb, Cu), Publication [Kokoku] No. 48497/81 [P, Mo, V, Sb (Fe, Ni, Mg, Ca, Al, W, Cu, Pb, Cr)], and U.S. Pat. No. 4,240,930 (P, Mo, Cu, Sb, Cs). However, these are not always adequate as industrial catalysts as they all have major drawbacks, such as poor reaction yields, rapid loss of catalytic activity with time, and excessively high reaction temperature.

SUMMARY OF THE INVENTION

Upon conducting extensive research aimed at improving existing methods of catalyst preparation, we discovered a novel process for the preparation of an excellent catalyst that is effective at lower reaction temperatures than catalysts prepared by prior art methods, and which gives high yields of unsaturated carboxylic acids.

DETAILED DESCRIPTION OF THE INVENTION

According to the present invention, in a process for preparing a catalyst for the production of unsaturated carboxylic acids, the catalyst being a multi-component catalyst containing at least phosphorus, molybdenum, and antimony in the catalyst composition, there is provided the improvement which comprises making use of antimony trioxide having an average particle size of not more than 0.2 micron as a starting material.

Use of the catalyst obtained by the process disclosed here makes possible the advantageous production of unsaturated carboxylic acids from the corresponding unsaturated aldehydes, and in particular acrylic acid or methacrylic acid from acrolein or methacrolein.

The atomic ratios of the phosphorus, antimony, and other elements present in the catalyst obtained by the present process should preferably lie within the following ranges, based on a value of 12 for molybdenum: phosphorus, 0.3 to 3; antimony, 0.05 to 3; alkali metals and thallium combined, 0 to 3; all other components combined, 0 to 10. Potassium, rubidium, and cesium are especially favorable as the alkali metals. Other elements that may serve as components of the catalyst include vanadium, silver, magnesium, zinc, selenium, tellurium, arsenic, copper, germanium, nickel, silicon, rhodium, tungsten, boron, tantalum, chromium, barium, tin, iron, and the like.

In the present invention, antimony trioxide having an average particle size of not more than 0.2 micron must be used as the starting material. If the starting material has an average particle size larger than this, catalyst with a superior performance cannot be obtained. The preferable range in the average particle size is 0.1 to 0.01 micron. The average particle sizes given here are the values obtained by measurement using an electron microscopy or a BET adsorption method. The average particle size of most commercially available industrial antimony trioxide ranges from 0.5 to 7 micron. This may be used after pulverizing to an average particle size of not more than 0.2 micron. Various methods exist for reducing coarser antimony trioxide to the desired particle size, examples of which include the classification of commercially available powder using a sieve of the required pore size, and an evaporation process in which antimony metal is evaporated to fine particles with an electrical arc and simultaneously converted into the trioxide.

Nitrates, ammonium salts, halides, oxides, and the like compounds of the various elements may be employed as the starting materials used for preparing the catalyst.

When working the invention, starting materials for the catalyst excluding the antimony trioxide is first dissolved or dispersed in water. The antimony trioxide may be added after this starting material mixture has been heated and the water driven off, but it is preferable to first add antimony trioxide to the mixture and stir thoroughly, then heat and drive off the water. The desired catalyst may be obtained by heat treatment, under a stream of air, of the solid thus obtained.

The catalyst prepared by means of the present process may be supported on inert carriers such as silica, alumina, silica/alumina, and silicon carbide, or used after dilution with any of these materials.

The catalyst of the invention is generally used in a fixed bed, but may be used also in a fluidized bed. The concentration of unsaturated aldehyde in the feedstock gas may be varied over a wide range, but a concentration of from 1 to 20% by volume, and particularly 3 to 10% by volume is preferable. Although using ordinary air as the oxygen source is economical, air enriched with pure oxygen may also be used. The oxygen concentration within the feedstock gas is represented as the molar ratio with respect to unsaturated aldehyde, a value of which should preferably range from 0.3 to 4, and especially 0.4 to 2.5. The feedstock gas ma be diluted by the addition of inert gases such as nitrogen, steam, carbon dioxide, and the like. The reaction pressure should range from atmospheric pressure to several atmospheres, and the reaction temperature should be from 240° to 450° C., and preferably from 260° to 400° C.

The conversion (%) of unsaturated aldehyde, and the selectivity (%) for and single-pass yield (%) of the unsaturated carboxylic acid formed, which are used in the following examples are defined below:

$$\text{Conversion (\%) of unsaturated aldehyde} = \frac{\text{moles of unsaturated aldehyde that reacted}}{\text{moles of unsaturated aldehyde fed}} \times 100$$

$$\text{Selectivty (\%) for unsaturated carboxylic acid} = \frac{\text{moles of unsaturated carboxylic acid produced}}{\text{moles of unsaturated aldehyde that reacted}} \times 100$$

lyst was $P_1Mo_{12}V_{0.6}As_{0.1}Cu_{0.1}Sn_1Rb_1Sb_{0.1}$. Using this catalyst, a reaction was conducted under the same reaction conditions as in Example 1 at a reaction temperature of 300° C. The results are given in the table below.

COMPARATIVE EXAMPLE 6

A catalyst having the same composition as in Example 6 was prepared using antimony trioxide with an average particle size of 3 microns. This catalyst was used in a reaction conducted under the same conditions as in Example 1 at a reaction temperature of 300° C. The results are given in the table below.

EXAMPLE 7

A catalyst was prepared in the same way as Example 2 using antimony trioxide with an average particle size of 0.03 micron. The composition of the resulting catalyst was $P_1Mo_{12}V_{0.5}Mg_1Te_{0.6}Si_{0.2}K_{0.8}Cs_{0.3}Sb_{0.7}$. Using this catalyst, a reaction was conducted under the same reaction conditions as in Example 1 at a reaction temperature of 295° C. The results are given in the table below.

COMPARATIVE EXAMPLE 7

A catalyst having the same composition as in Example 7 was prepared using antimony trioxide with an average particle size of 3 microns. This catalyst was used in a reaction conducted under the same conditions as in Example 1 at a reaction temperature of 295° C. The results are given in the table below.

EXAMPLE 8

Using the catalyst prepared in Example 2, a gas mixture consisting of acrolein (5% by volume), oxygen (10%), steam (30%), and nitrogen (55%) was introduced into a catalyst layer for a contact time of 3.6 seconds at a reaction temperature of 290° C. The results were an acrolein conversion of 9.18%, a selectivity for acrylic acid of 90.3%, and a single-pass yield of acrylic acid of 82.9%.

EXAMPLE 10

A reaction was conducted using the catalyst in Comparative Example 2 under the same reaction conditions as in Example 8, giving an acrolein conversion of 90.5%, a selectivity for acrylic acid of 89.0%, and a single-pass yield of acrylic acid of 80.5%.

We claim:

1. In a process for producing an unsaturated carboxylic acid which comprises contacting a corresponding unsaturated aldehyde with a mixture of oxygen, nitrogen and steam in the presence of a multi-component oxide catalyst selected from the group consisting of $P_{1.5}Mo_{12}V_{0.5}Cu_{0.5}Ge_{0.5}K_1Sb_{0.8}$, $P_{1.6}Mo_{12}V_{0.8}Cu_{0.2}Se_{0.2}Ag_{0.1}Ba_{0.1}Rb_1Sb_{0.5}$ and $P_2Mo_{12}W_{0.2}Fe_{0.5}B_{0.2}Ni_{0.5}Cs_2Sb_1$, wherein the method for producing said catalyst comprises first dissolving or dispersing the catalyst components in water, except for antimony trioxide, subsequently adding antimony trioxide and driving off the water either before or after the antimony triode is added, the improvement comprising using antimony trioxide having an average particle size of not more than 0.2 micron as a starting material.

2. The process according to claim 1 wherein said carboxylic acid is methacrylic acid and said aldehyde is methacrolein.

TABLE

| | Average particle size of antimony trioxide ($\mu$) | Reaction temperature (°C.) | Conversion of methacrolein (%) | Selectivity for methacrylic acid (%) | Single-pass yield of methacrylic acid (%) |
|---|---|---|---|---|---|
| Example 3 | 0.03 | 290 | 84.0 | 89.0 | 74.8 |
| Comparative Example 3 | 2 | 290 | 82.5 | 88.6 | 73.1 |
| Example 4 | 0.1 | 275 | 83.3 | 84.1 | 70.1 |
| Comparative Example 4 | 0.7 | 275 | 81.0 | 83.2 | 67.4 |
| Example 5 | 0.05 | 340 | 80.1 | 84.9 | 68.0 |
| Comparative Example 5 | 4 | 340 | 76.5 | 83.4 | 63.8 |
| Example 6 | 0.08 | 300 | 83.2 | 86.8 | 72.2 |
| Comparative Example 6 | 3 | 300 | 81.0 | 86.1 | 69.7 |
| Example 7 | 0.03 | 295 | 85.4 | 83.6 | 71.4 |
| Comparative Example 7 | 3 | 295 | 83.3 | 82.5 | 68.7 |

* * * * *